United States Patent [19]

Ibrahim et al.

[11] Patent Number: 4,985,236

[45] Date of Patent: * Jan. 15, 1991

[54] TRIPOLYPHOSPHATE-CONTAINING ANTI-CALCULUS TOOTHPASTE

[75] Inventors: Nader Ibrahim, Hackettstown; Jeanette L. Sodano, Clifton, both of N.J.

[73] Assignee: Beecham Inc., Clifton, N.J.

[ * ] Notice: The portion of the term of this patent subsequent to May 8, 2007 has been disclaimed.

[21] Appl. No.: 407,336

[22] Filed: Sep. 14, 1989

Related U.S. Application Data

[63] Continuation-in-part of Ser. No. 348,805, May 8, 1989, Pat. No. 4,923,684.

[51] Int. Cl.$^5$ .......................... A61K 9/16; A61K 9/18
[52] U.S. Cl. ........................................ 424/52; 424/57
[58] Field of Search ...................................... 424/52, 57

[56] References Cited

U.S. PATENT DOCUMENTS

| | | | |
|---|---|---|---|
| 3,934,002 | 1/1976 | Haefele | 424/54 |
| 4,046,872 | 9/1977 | Mitchell | 424/52 |
| 4,075,317 | 2/1978 | Mitchell | 424/52 |
| 4,244,931 | 1/1981 | Jarvis et al. | 424/57 |
| 4,247,526 | 1/1981 | Jarvis et al. | 424/57 |
| 4,267,167 | 5/1981 | Weitzman et al. | 424/52 |
| 4,272,509 | 6/1981 | Wason | 424/49 |
| 4,340,583 | 7/1982 | Wason | 424/52 |
| 4,420,312 | 12/1983 | Wason | 424/52 |
| 4,421,527 | 12/1983 | Wason | 424/52 |
| 4,460,565 | 7/1984 | Westrate et al. | 424/52 |
| 4,515,772 | 5/1985 | Parran, Jr. | 424/52 |
| 4,568,534 | 2/1986 | Stier et al. | 424/52 |
| 4,627,977 | 12/1986 | Gaffar | 424/52 |
| 4,806,342 | 2/1989 | Gaffar | 424/52 |
| 4,808,400 | 2/1989 | Gaffar et al. | 424/52 |
| 4,808,401 | 2/1989 | Gaffar et al. | 423/52 |
| 4,842,847 | 6/1989 | Amjad | 424/52 |
| 4,889,713 | 12/1989 | Gaffar et al. | 424/52 |
| 4,892,724 | 1/1990 | Amjad | 424/52 |
| 4,892,725 | 1/1990 | Amjad | 424/52 |
| 4,923,684 | 5/1990 | Ibrahim et al. | 424/52 |

FOREIGN PATENT DOCUMENTS

| | | |
|---|---|---|
| 236290 | 9/1987 | European Pat. Off. . |
| 0254452 | 1/1988 | European Pat. Off. . |
| 295116 | 12/1988 | European Pat. Off. . |
| 61-036211 | 2/1986 | Japan . |
| 2188548 | 10/1987 | United Kingdom . |
| 2200551 | 8/1988 | United Kingdom . |

OTHER PUBLICATIONS

Takahashi et al., (Lion) Ca. 110:141334p (1988), of JP 63-1, 41920, A2 Jun. 14, 1988.
Briner and Francis, Calc. Tiss. Res., 11, pp. 10–22, (1973).

*Primary Examiner*—Shep K. Rose
*Attorney, Agent, or Firm*—Jacobs & Jacobs

[57] ABSTRACT

A storage stable anticalculus toothpaste comprising at least about 4%, by weight, based on the total weight of the toothpaste, of a water-soluble alkali metal tripolyphosphate, a phosphatase enzyme inhibitor consisting of a fluoride ion source in an amount sufficient to supply from about 25 ppm to about 3500 ppm of fluoride ion, a silica or plastics dental abrasive and an orally acceptable vehicle, the toothpaste having a pH of from about 8 to about 10.

20 Claims, No Drawings

TRIPOLYPHOSPHATE-CONTAINING ANTI-CALCULUS TOOTHPASTE The present application is a continuation-in-part of our copending application Ser. No. 348,805, filed May 8, 1989 now U.S. Pat. No. 4,923,684, which is incorporated herein by reference thereto.

The present invention relates to toothpaste containing a water-soluble alkali metal tripolyphosphate as a dental calculus inhibitor, a phosphatase enzyme inhibitor consisting of a source of fluoride ion and a dental abrasive.

U.S. Pat. No. 4,515,772, issued May 7, 1985 to Parran et al, discloses oral anti-calculus compositions, including toothpastes, comprising a dialkali metal pyrophosphate or a mixture of dialkali metal and tetraalkali metal pyrophosphates in combination with a fluoride ion source.

U.S. Pat. No. 4,627,977, issued Dec. 9, 1986 to Gaffar et al, discloses oral compositions, including toothpaste, comprising an effective anti-calculus amount of one or a mixture of linear molecular dehydrated polyphosphate salts as an anti-calculus agent and as an inhibitor against enzymatic hydrolysis of the anti-calculus agent in saliva, an amount of a fluoride ion source sufficient to supply about 25-2000 ppm of fluoride ions in combination with about 0.05-3% of a synthetic anionic linear polymeric polycarboxylate having a molecular weight of about 2000 to about 1 million. Among the polyphosphates described in Gaffar et al is sodium tripolyphosphate (STP).

European Patent Application No. 236,290 discloses a dentifrice, including toothpaste, comprising an abrasive, particularly essentially insoluble calcium pyrophosphate, and an effective amount of a soluble pyrophosphate or tripolyphosphate as an anti-calculus agent. EPO No. 236,290 discloses toothpastes containing STP as the anti-calculus agent.

European patent application No. 295,116 discloses oral compositions for inhibiting dental calculus containing an anti-calculus agent in the form of 0.5-7 wt % of a linear molecularly dehydrated polyphosphate salt and 0.05-2.0% of a zinc salt. STP is disclosed as a suitable polyphosphate salt.

Despite the proposals in the prior art to use STP as an anti-calculus agent, so far as we are aware no anti-calculus toothpaste has been commercially available using STP as the anti-calculus agent. The Gaffar et al patent and EPO No. 295,116 do not provide any data on the storage stability of their STP-containing toothpastes. EPO No. 236,290 does provide storage stability data on two toothpastes containing insoluble calcium pyrophosphate as an abrasive, STP and sodium monofluorophosphate. These data show that under accelerated aging conditions, both STP-containing toothpastes lost about one-third of the original STP present, which would be unsuitable for a commercial product.

The present invention provides a storage stable tripolyphosphate salt-containing anti-calculus toothpaste by proceeding against the teachings in the prior art. In accordance with the present invention, a storage stable anti-calculus toothpaste is provided comprising relatively large amounts of a water-soluble alkali metal tripolyphosphate salt, contrary to the expressed preference for smaller amounts of STP in EPO No. 295,116, a high pH, contrary to the expressed preference for lower pH's in EPO No. 236,290, and a phosphatase enzyme inhibitor consisting of a fluoride ion source, contrary to the teaching of the Gaffar et al patent. The anti-calculus toothpaste formulated according to the present invention has unexpectedly superior storage stability than otherwise identical toothpastes formulated at lower pH or lower concentrations of tripolyphosphate salt.

In particular, the present invention provides a toothpaste comprising at least about 4% by weight, based on the total weight of the toothpaste, of a water-soluble alkali metal tripolyphosphate, a phosphatase enzyme inhibitor consisting of a fluoride ion source in an amount sufficient to supply from about 25 ppm to about 3500 ppm of fluoride ion, a dental abrasive such as silica or plastics particles and an orally acceptable vehicle, the toothpaste having a pH of from about 8 to about 10.

The following illustrates the unexpected superiority of the present invention.

Toothpastes A, B, C and D were prepared using a silica dental abrasive, STP and a phosphatase inhibitor consisting of sodium fluoride in an amount to provide 1100 ppm fluoride in an aqueous orally acceptable vehicle. The amounts of STP and the pH of the toothpastes were varied as shown in the Table below:

TABLE

| Toothpaste* | Percent STP As % of Initial STP After | | | |
|---|---|---|---|---|
| | 1 year | 2 years | 3 years | 4 years |
| A (pH 9/4.3% STP) | 98 | 96 | 94 | 91 |
| B (pH 7/4.3% STP) | 96 | 93 | 89 | 85 |
| C (pH 9/3.0% STP) | 90 | 80 | 69 | 59 |
| D (pH 7/2.8% STP) | 85 | 70 | 55 | 39 |

*The pH's reported are nominal values.

As can be seen, toothpaste A containing the high amount of STP and the high pH was the most stable of the four toothpastes. The data presented in the Table were derived from storage stability tests on actual samples of the four toothpastes, with the storage stability data regressed to provide predicted stability over four years of storage at room temperature with a confidence level of 95%. The storage stability data in the Table show that the use of either a large amount of STP (B) or a high pH (C) is not sufficient to impart excellent storage stability. Unexpectedly, the use of a large amount of STP and a high pH in combination with a silica dental abrasive and a phosphatase inhibitor consisting of a fluoride ion source will provide sufficient storage stability required for a commercial toothpaste.

The tripolyphosphate salt used in the present invention can be any of the water-soluble alkali metal tripolyphosphates, preferably sodium tripolyphosphate and/or potassium tripolyphosphate, and may be used in its hydrated or unhydrated form. The amount of the tripolyphosphate salt will be at least about 4%, preferably from about 4 to about 6%, by weight, based on the total weight of the toothpaste. While amounts greater than about 6% of the tripolyphosphate salt can be used, it is not economical to use larger amounts of the tripolyphosphate salt than are necessary to provide the desired anti-calculus effect.

The toothpaste of the present invention will be formulated to have a pH of from about 8 to about 10, preferably from about 8 to about 9. As used throughout this specification and the appended claims, all references to pH are to the pH of the toothpaste measured without dilution of the toothpaste. Sodium hydroxide or other base suitable for use in compositions intended for use in the oral cavity may be used to adjust the pH of the toothpaste to the desired pH level.

It is discussed in the prior art that polyphosphate anti-calculus agents are subject to hydrolysis by phosphatase enzymes in saliva. Hence, the toothpaste according to the invention contains a phosphatase inhibitor consisting of a fluoride ion source. Numerous sources of fluoride ion are well known for use in toothpastes, such as alkali metal fluorides, preferably sodium fluoride alkali metal monofluorophosphates, stannous fluoride and the like. Preferably, however the fluoride ion source is an alkali metal fluoride, most preferably sodium fluoride, since this appears to provide enhanced storage stablility as compared to other fluoride ion sources. In addition to serving as a phosphatase enzyme inhibitor, the fluoride ion source will also provide an anticaries effect. Preferably, the fluoride ion source will be used in an amount to provide an anticaries effective amount and a phosphatase enzyme inhibiting amount, such as an amount sufficient to provide from about 25 ppm to about 3500 ppm, preferably about 1100 ppm, fluoride.

Any suitable silica or plastics dental abrasive may be used in the toothpaste according to the present invention. Silica dental abrasives are well known, are commercially available and generally have an average particle size ranging between about 0.1 to about 30 microns, such as from about 5 to about 15 microns. Silica dental abrasives useful in the present invention include those marketed by the J. M. Huber Corporation under the trade name "Zeodent" and the silica xerogels marketed by the W. R. Grace and Company, Davison Chemical Division under the trade name "Syloid". U.S. Pat. Nos. 3,358,230 and 3,862,307 describe silica dental abrasives that are useful in the toothpastes according to the present invention.

Plastics dental abrasives are well known and are described in, for example, U.K. Patents Nos. 939,230, 995,351 and 1,055,784, and U.S. Pat. No. 3,151,027.

Generally, an amount of the dental abrasive suitable for use in the toothpaste of the present invention will be empirically determined to provide an acceptable level of cleaning and polishing, in accordance with techniques well known in the art. Suitably, the toothpaste of the present invention will contain from about 5 to about 30% by weight of the dental abrasive.

In formulating the toothpaste according to the present invention, the tripolyphosphate salt, dental abrasive and phosphatase inhibitor are incorporated into an orally acceptable dental vehicle, which may be anhydrous but preferably is an aqueous orally acceptable dental vehicle, to form a storage stable semi-solid extrudable material useful as a toothpaste. Preferably, the tripolyphosphate salt is in powder form when incorporated into the vehicle, as this tends to enhance the stability of the resulting toothpaste. As is conventional, the orally acceptable dental vehicle will comprise a binder or thickener, such as natural and synthetic gums, e.g., xanthan gum, carageenates, alginates, cellulose ethers and esters, silica and the like. In formulating the preferred aqueous orally acceptable dental vehicle, a suitable humectant is preferably employed, such as glycerin, sorbitol, propylene glycol or a polyethylene glycol.

In addition, the orally acceptable dental vehicle may include optional ingredients, such as detergents, sweeting agents, flavoring agents, anticaries agents in addition to the fluoride ion source provided as the phosphatase inhibitor, anti-plaque agents, antimicrobial agents such as triclosan, tooth desensitizing agents, coloring agents and pigments. Useful detergents include the water-soluble salts of alkyl sulfates having from 10 to 18 carbon atoms in the alkyl moiety, such as sodium lauryl sulfate, but other anionic detergents as well as non-ionic, zwitter-ionic, cationic and amphoteric detergents may also be used.

When the preferred aqueous orally acceptable dental vehicle is employed, the toothpaste of the present invention suitably contains from about 10 to about 80% humectant, from about 0.25 to about 5% detergent, from 0 to about 2% sweeteners and flavoring agents together with water and an effective amount of binders and thickening agents, such as from about 0.1% to about 12%, to provide the toothpaste of the invention with the desired stability and flow characteristics.

Conventional manufacturing techniques are employed to prepare the toothpaste according to the present invention. The toothpaste of the present invention may be prepared in the form of a paste of a uniform color or in the form of a striped toothpaste. A suitable aparatus for filling toothpaste tubes with striped toothpaste is described in U.K. Patent Specification No. 962,757. In accordance with this patent, toothpastes of different colors are fed through separate tubes of a bundle of tubes that is inserted into a toothpaste container and gradually moved relative to the container as the container is filled.

The toothpaste of the present invention is used in a conventional manner by applying the toothpaste to the teeth. Brushing the teeth with the toothpaste of the present invention inhibits the formation of dental calculus in persons susceptible to the formation of dental calculus.

The present invention is illustrated in terms of its preferred embodiments in the accompanying Example. All parts and percentages referred to in this specification and the appended claims are by weight based upon the total weight of the toothpaste, unless otherwise specified.

EXAMPLE

A toothpaste was prepared from the following ingredients, the STP being in powder form when combined with the other ingredients.

| Ingredients | % W/W |
| --- | --- |
| PEG-8(CTFA) | 3.000 |
| Xanthan Gum | 0.700 |
| D&C Red #30 Lake | 0.017 |
| FD&C Blue #1 (0.2%) | 0.168 |
| Yellow #10 (0.02%) | 0.137 |
| Deionized Water | 24.206 |
| Sodium Fluoride | 0.243 |
| Sorbitol (70%) | 29.609 |
| Sodium Saccharin | 0.214 |
| Hydrated Silica (Thickener) | 8.000 |
| Hydrated Silica (Dental Abrasive) | 14.000 |
| Titanium Dioxide | 0.956 |
| Glycerin 99% | 10.000 |
| Sodium Tripolyphosphate (Food Grade)* | 5.000 |
| Sodium Hydroxide (25%) | 1.800 |
| Flavor | 0.800 |
| Sodium Lauryl Sulfate | 1.150 |
| TOTAL | 100.000% |

*Food grade STP has a nominal purity of 92%.

In these formulas, the humectant was composed of PEG-8 (polyethylene glycol), sorbitol and glycerin, the binder and thickening agents were xanthan gum and hydrated silica.

The toothpaste had an initial STP content of about 4.3% and an initial pH of about 8.4.

Toothpaste prepared in accordance with this Example exhibited excellent storage stability. Its predicted storage stability was such that about 91% of the initial content of STP would be present after four years of storage at room temperature with a confidence level of 95%.

We claim:

1. A toothpaste, which comprises at least about 4% by weight, based on the total weight of the toothpaste, of a water-soluble alkali metal tripolyphosphate, a phosphatase enzyme inhibitor consisting of a fluoride ion source in an amount sufficient to supply from about 25 ppm to about 3500 ppm of fluoride ion, a silica or plastics dental abrasive and an orally acceptable vehicle, the toothpaste having a pH of from about 8 to about 10.

2. The toothpaste according to claim 1, wherein said water-soluble alkali metal tripolyphosphate is sodium tripolyphosphate.

3. The toothpaste according to claim 1, wherein said water-soluble alkali metal tripolyphosphate is present in an amount of from about 4 to 6%, by weight, based on the total weight of the toothpaste.

4. The toothpaste according to claim 1, wherein said pH is from about 8 to about 9.

5. The toothpaste according to claim 1, wherein said fluoride ion source is an alkali metal fluoride.

6. The toothpaste according to claim 5, wherein said alkali metal fluoride is sodium fluoride.

7. The toothpaste according to claim 1, wherein said orally acceptable vehicle is an aqueous orally acceptable vehicle.

8. The toothpaste according to claim 7, wherein said aqueous orally acceptable vehicle comprises a humectant.

9. A toothpaste, which comprises at least about 4%, by weight, based on the total weight of the toothpaste, of a water-soluble alkali metal tripolyphosphate, a phosphatase enzyme inhibitor consisting of a fluoride ion source in an amount sufficient to supply from about 25 ppm to about 3500 ppm of fluoride ion, from about 5 to about 30% by weight, based on the total weight of the toothpaste, of a silica dental abrasive and an orally acceptable vehicle comprising a binder or thickener, the toothpaste having a pH of from about 8 to about 10.

10. The toothpaste according to claim 9, wherein said water-soluble alkali metal tripolyphosphate is sodium tripolyphosphate.

11. The toothpaste according to claim 9, wherein said water-soluble alkali metal tripolyphosphate is present in an amount of from about 4 to about 6%, by weight, based on the total weight of the toothpaste.

12. The toothpaste according to claim 9, wherein said pH is from about 8 to about 9.

13. The toothpaste according to claim 9, wherein said fluoride ion source is an alkali metal fluoride.

14. The toothpaste according to claim 13, wherein said alkali metal fluoride is sodium fluoride.

15. The toothpaste according to claim 9, wherein said orally acceptable vehicle is an aqueous orally acceptable vehicle.

16. The toothpaste according to claim 15, wherein said aqueous orally acceptable vehicle comprises a humectant.

17. A method of treating humans who are susceptible to the formation of dental calculus, which comprises applying to the teeth of such calculus formers a toothpaste according to claim 1, thereby to inhibit formation of dental calculus.

18. A method of treating humans who are susceptible to the formation of dental calculus, which comprises applying to the teeth of such calculus formers a toothpaste according to claim 9, thereby to inhibit formation of dental calculus.

19. A method of preparing the toothpaste according to claim 1, which comprises admixing said water-soluble tripolyphosphate in the form of a powder with said phosphatase inhibitor, said dental abrasive and said orally acceptable vehicle, and adding an amount of a base suitable for use in the oral cavity to provide a pH of from about 8 to about 10.

20. A method of preparing the toothpaste according to claim 9, which comprises admixing said water-soluble tripolyphosphate in the form of a powder with said phosphatase inhibitor, said silica dental abrasive and said orally acceptable vehicle, and adding an amount of a base suitable for use in the oral cavity to provide a pH of from about 8 to about 10.

* * * * *